United States Patent
Kishino et al.

(10) Patent No.: US 12,241,103 B2
(45) Date of Patent: Mar. 4, 2025

(54) PRODUCTION SYSTEM AND METHOD OF PRODUCTION FOR ORGANIC COMPOUND OR MICROORGANISM

(71) Applicants: AJINOMOTO CO., INC., Tokyo (JP); TOKYO INSTITUTE OF TECHNOLOGY, Tokyo (JP)

(72) Inventors: Mitsuhiro Kishino, Kanagawa (JP); Hiroyuki Kojima, Kanagawa (JP); Hideo Hosono, Tokyo (JP); Michikazu Hara, Tokyo (JP); Masaaki Kitano, Tokyo (JP); Toshiharu Yokoyama, Tokyo (JP); Toru Numaguchi, Tokyo (JP); Munenobu Ito, Kanagawa (JP); Kazuteru Yamada, Kanagawa (JP); Hiromi Noguchi, Kanagawa (JP)

(73) Assignees: Ajinomoto Co., Inc., Tokyo (JP); Tokyo Institute of Technology, Tokyo (JP)

( * ) Notice: Subject to any disclaimer, the term of this patent is extended or adjusted under 35 U.S.C. 154(b) by 614 days.

(21) Appl. No.: 17/019,666

(22) Filed: Sep. 14, 2020

(65) Prior Publication Data
US 2020/0407762 A1 Dec. 31, 2020

Related U.S. Application Data

(60) Division of application No. 15/675,113, filed on Aug. 11, 2017, now Pat. No. 10,808,267, which is a (Continued)

(30) Foreign Application Priority Data

Feb. 17, 2015 (JP) ................. 2015-028959

(51) Int. Cl.
*C12P 13/14* (2006.01)
*B01J 23/02* (2006.01)
(Continued)

(52) U.S. Cl.
CPC ............... *C12P 13/14* (2013.01); *B01J 23/02* (2013.01); *B01J 23/04* (2013.01); *B01J 23/462* (2013.01);
(Continued)

(58) Field of Classification Search
None
See application file for complete search history.

(56) References Cited

U.S. PATENT DOCUMENTS 3,770,658 A * 11/1973 Ozaki .................. B01J 23/16
502/178
3,897,303 A 7/1975 Sherk et al.
(Continued)

FOREIGN PATENT DOCUMENTS

CN 1329574 A 1/2002
CN 101186934 A 5/2008
(Continued)

OTHER PUBLICATIONS

Japanese Office Action from Japanese Patent App. No. 2020-192494 dated Feb. 1, 2022 with English Machine Translation thereof.
(Continued)

*Primary Examiner* — William H. Beisner
(74) *Attorney, Agent, or Firm* — Cermak & McGowan LLP; Shelly Guest Cermak

(57) ABSTRACT

Provided is a novel production system that does not involve, or can minimize, the transport of liquid ammonia in the production of an organic compound or the production of a microorganism by microbial fermentation. A production system for an organic compound or a microorganism includes: an ammonia synthesis apparatus in which an ammonia-containing gas is synthesized by reaction of a source gas containing hydrogen and nitrogen in the presence of a supported ruthenium catalyst; and a culture apparatus
(Continued)

that cultures a microorganism having organic compound productivity using ammonia originating from the ammonia-containing gas obtained by using the ammonia synthesis apparatus.

7 Claims, 2 Drawing Sheets

Related U.S. Application Data continuation of application No. PCT/JP2016/054611, filed on Feb. 17, 2016.

(51) Int. Cl.

| | |
|---|---|
| B01J 23/04 | (2006.01) |
| B01J 23/46 | (2006.01) |
| B01J 23/58 | (2006.01) |
| B01J 35/00 | (2006.01) |
| B01J 37/02 | (2006.01) |
| C01C 1/04 | (2006.01) |
| C12M 1/00 | (2006.01) |
| C12N 1/20 | (2006.01) |
| C12P 13/08 | (2006.01) |

(52) U.S. Cl.
CPC .............. *B01J 23/58* (2013.01); *B01J 35/19* (2024.01); *B01J 37/0221* (2013.01); *C01C 1/0411* (2013.01); *C01C 1/0417* (2013.01); *C01C 1/0458* (2013.01); *C01C 1/0476* (2013.01); *C12M 23/58* (2013.01); *C12M 43/00* (2013.01); *C12N 1/20* (2013.01); *C12P 13/08* (2013.01); *C01B 2203/0233* (2013.01); *C01B 2203/025* (2013.01); *C01B 2203/0283* (2013.01); *C01B 2203/04* (2013.01); *C01B 2203/0475* (2013.01); *Y02P 20/52* (2015.11)

(56) References Cited

U.S. PATENT DOCUMENTS

| | | | | |
|---|---|---|---|---|
| 4,021,304 | A * | 5/1977 | Shimamatsu | C12N 1/32 435/921 |
| 4,242,458 | A | 12/1980 | Child et al. | |
| 4,671,893 | A | 6/1987 | Pinto | |
| 6,955,797 | B1 | 10/2005 | Speth | |
| 7,514,058 | B1 | 4/2009 | Hitzman et al. | |
| 2002/0004451 | A1 | 1/2002 | Muhler et al. | |
| 2006/0036062 | A1 | 2/2006 | Ramakrishna et al. | |
| 2006/0154345 | A1 | 7/2006 | Rayapati et al. | |
| 2007/0243590 | A1 | 10/2007 | Takeshita et al. | |
| 2008/0090272 | A1 | 4/2008 | Rayapati et al. | |
| 2009/0239268 | A1 | 9/2009 | Okutani et al. | |
| 2010/0273221 | A1 | 10/2010 | Takeshita et al. | |
| 2012/0149072 | A1 | 6/2012 | Takeshita et al. | |
| 2013/0183224 | A1 | 7/2013 | Hosono et al. | |
| 2014/0322124 | A1 | 10/2014 | Izaki et al. | |
| 2015/0010962 | A1 | 1/2015 | Takeshita et al. | |
| 2015/0010963 | A1 | 1/2015 | Takeshita et al. | |
| 2015/0259716 | A1 | 9/2015 | Takeshita et al. | |
| 2017/0283271 | A1 * | 10/2017 | Sakurai | B01D 53/002 |

FOREIGN PATENT DOCUMENTS

| | | | | | |
|---|---|---|---|---|---|
| CN | 102815721 | A | * | 12/2012 | |
| CN | 103237599 | A | | 8/2013 | |
| GB | 2145702 | A | * | 4/1985 | ........... C01C 1/0458 |
| JP | 47-002917 | A | | 2/1972 | |
| JP | 47-036639 | B | | 9/1972 | |
| JP | 56-124496 | A | | 9/1981 | |
| JP | 61-192295 | A | | 8/1986 | |
| JP | 10-066567 | A | | 3/1998 | |
| JP | 2000044230 | A | * | 2/2000 | |
| JP | 2001-069999 | A | | 3/2001 | |
| JP | 2002012420 | A | * | 1/2002 | |
| JP | 2002-052341 | A | | 2/2002 | |
| JP | 2003-020221 | A | | 1/2003 | |
| JP | 2003-506030 | A | | 2/2003 | |
| JP | 2003-506037 | A | | 2/2003 | |
| JP | 2003-267725 | A | | 9/2003 | |
| JP | 2006-225210 | A | | 8/2006 | |
| JP | 2007-538132 | A | | 12/2007 | |
| JP | 2008-247654 | A | | 10/2008 | |
| JP | 2010-017082 | A | | 1/2010 | |
| JP | 2011-521134 | A | | 7/2011 | |
| JP | 2011-246311 | A | | 12/2011 | |
| JP | 2013-111563 | A | | 6/2013 | |
| WO | WO91/09306 | A2 | | 2/2001 | |
| WO | WO-0109306 | A2 | * | 2/2001 | ............. C12N 15/01 |
| WO | WO2006/038695 | A1 | | 4/2006 | |
| WO | WO2007/032265 | A1 | | 3/2007 | |
| WO | WO2011/008900 | A1 | | 1/2011 | |
| WO | WO2012/077658 | A1 | | 6/2012 | |

OTHER PUBLICATIONS

Hara, M., "Development of Novel Catalyst for Ammonium Synthesis by Electride—Quest for reaction going beyond Haber-Bosch process—," Chemistry Today 2013;505:32-36 with English language translation thereof.

Kasumi, T., "Chemical and Biological" (2014), vol. 52, No. 7, pp. 478-484.

Hirota, R., et al., "Molecular Biology of Ammonia-Oxidizing Bacteria," J. Environmen. Biotechnol. 2002;2(2):135-143, with partial English language translation.

Kitano, M., et al., "Ko-kassei Ammonia Gosei Shokubai no Kaihatsu," ("Development of Highly-Active Ammonia Synthesis Catalyst"); Kagaku Keizai, 2013, vol. 60, No. 2, pp. 73-77, with partial English language translation.

International Search Report and Written Opinion for PCT Patent App. No. PCT/JP2016/054611 (Mar. 22, 2016) with English language translation of ISR.

Extended European Search Report for European Patent App. No. 16752520.3 (Oct. 18, 2018).

Office Action from Chinese Patent App. No. 201680010598.X (Sep. 3, 2019) with English language translation thereof.

Waksman, S. A., et al., "Microorganisms Concerned in the Oxidation of Sulfur in the Soil," J. Bacteriol. 1922;7(2):239-256.

Office Action from Japanese Patent App. No. 2017-500721 (Mar. 31, 2020) with English language translation thereof.

Communication Pursuant to Article 94(3) EPC from European Patent App. No. 16752520.3 (Jul. 1, 2020).

Office Action from Japanese Patent App. No. 2020-192494 dated Oct. 11, 2022 with English language machine translation.

Office Action from Japanese Patent App. No. 2020-192494 dated Jul. 26, 2022 with English language machine translation.

* cited by examiner

PRODUCTION SYSTEM AND METHOD OF PRODUCTION FOR ORGANIC COMPOUND OR MICROORGANISM

This application is a Divisional of, and claims priority under 35 U.S.C. § 120 to U.S. patent application Ser. No. 15/675,113, filed Aug. 11, 2017, which was a Continuation of, and claims priority under 35 U.S.C. § 120 to, International Application No. PCT/JP2016/054611, filed Feb. 17, 2016, and claims priority therethrough under 35 U.S.C. § 119 to Japanese Patent Application No. 2015-028959, filed Feb. 17, 2015, the entireties of which are incorporated by reference herein.

BACKGROUND OF THE INVENTION

Field of the Invention

The present invention relates to a production system and a method of production for an organic compound or a microorganism.

Brief Description of the Related Art

Techniques for culturing microorganisms having the ability to produce organic compounds are widely reported in the literature. See WO 2006/038695, Japanese Patent Application Laid-open No. 2010-017082, and "Aminosan Hakko Gijutu no Keitouka Chousa", National Museum of Science and Nature, Gijutu no Keitouka Chousa Houkoku Vol. 11, Independent Administrative Agency National Museum of Science and Nature, Mar. 19, 2008, pp. 55-90, for example. The majority of amino acids in global distribution have been produced by fermentation methods for amino acids. Techniques are known that produce various kinds of organic compounds such as polysaccharides, proteins, antibiotics, alcohols, acrylamide, and diene compounds apart from amino acids by microbial fermentation, and research and development thereon are still currently being advanced.

In microbial fermentation, ammonia and nitrogen-containing compounds originating from ammonia, such as ammonium salts, urea, nitric acid, and nitrates, for example, are generally used as a nitrogen source and a pH adjuster (See "Hakko Kogaku no Kiso Jikkensitsu kara Kojo made", Gakkai Shuppan Senta, September of 1988, pp. 78-81).

SUMMARY OF THE INVENTION

The use of microbial fermentation for production of organic compounds is increasing globally, and the amount of ammonia used as the nitrogen source and as the pH adjuster also is increasing.

Ammonia is mainly produced by a large-scale production process, such as by the Haber-Bosch process. In the Haber-Bosch process, a source gas containing hydrogen and nitrogen reacts under high-temperature, high-pressure conditions at 400° C. to 600° C. and 20 MPa to 100 MPa using a doubly promoted iron catalyst obtained by adding a few percent by weight of $Al_2O_3$ and $K_2O$ to $Fe_3O_4$ to synthesize ammonia.

Global demand for ammonia for use as a raw material in production of various kinds of chemical products and fertilizers, apart from microbial fermentation, is increasing; and therefore, production plants for synthesizing ammonia are increasingly upsizing. The synthesis of ammonia by such a large-scale production process assumes that the resulting ammonia is liquefied and stored and is transported as liquid ammonia to ammonia consumption sites. In addition to the costs of ammonia synthesis itself, also required are costs associated with the storage, transport, and maintenance of liquid ammonia, and these prices tend to be high.

To scale up the microbial fermentation process, procurement of ammonia to be used as the nitrogen source and the pH adjuster in the large-scale process is necessary at a low price and in a sufficient amount.

It is an aspect of the present invention to provide a novel production system and a method of production that do not involve, or can minimize, the transport of liquid ammonia in the production of organic compounds by microbial fermentation.

In microorganism fermentation, microorganisms grow utilizing a carbon source, a nitrogen source, or the like. In that sense, it is an aspect of the present invention to provide a novel production system and a method of production that do not involve, (or can minimize, the transport of liquid ammonia in the production of microorganisms.

It is an aspect of the present invention to provide a production system useful for reacting a source gas and a ruthenium catalyst to produce an organic compound or a microorganism, the production system comprising: A) an ammonia synthesis apparatus configured to react a source gas comprising hydrogen and nitrogen in the presence of a ruthenium catalyst and a support, wherein an ammonia-containing gas is synthesized; and B) a culture apparatus that is configured to culture a microorganism able to produce an organic compound using ammonia originating from said ammonia-containing gas.

It is a further aspect of the present invention to provide the system as described above, wherein said ammonia synthesis apparatus is configured to react the source gas under conditions comprising a reaction temperature of 530° C. or lower and a reaction pressure of 30 MPa or lower.

It is a further aspect of the present invention to provide the system as described above, further comprising an ammonia concentration apparatus that is configured to concentrate the ammonia from the ammonia-containing gas.

It is a further aspect of the present invention to provide the system as described above, further comprising a recycle apparatus that is configured to recover unreacted hydrogen and nitrogen following said reaction in the ammonia synthesis apparatus, and is also configured to return said unreacted hydrogen and nitrogen to be reacted again in the ammonia synthesis apparatus.

It is a further aspect of the present invention to provide the system as described above, wherein the recycle apparatus comprises a dehydrator and/or a drier configured to remove water from said unreacted hydrogen and nitrogen.

It is a further aspect of the present invention to provide the system as described above, wherein the production system is configured to produce ammonia water using the ammonia originating from said ammonia-containing gas and is also configured to culture a microorganism able to produce an organic compound using said ammonia water.

It is a further aspect of the present invention to provide the system as described above, wherein the production system is configured to: produce ammonia water using the ammonia originating from said ammonia-containing gas, recover ammonia gas from said ammonia water, and culture a microorganism able to produce an organic compound using said ammonia gas.

It is a further aspect of the present invention to provide the system as described above, wherein ammonia is used as a nitrogen source or a pH adjuster in the culture apparatus.

It is a further aspect of the present invention to provide the system as described above, wherein the microorganism is able to produce an organic compound selected from the group consisting of amino acids, organic acids, polysaccharides, proteins, antibiotics, and alcohols.

It is a further aspect of the present invention to provide the system as described above, wherein the microorganism is a bacterium or a fungus.

It is a further aspect of the present invention to provide a method of production for a produce selected from the group consisting of an organic compound and a microorganism, the method comprising the steps of: (A) reacting a source gas comprising hydrogen and nitrogen in the presence of a ruthenium catalyst and a support, wherein an ammonia gas is synthesized; and (B) culturing a microorganism able to produce an organic compound using ammonia originating from said ammonia-containing gas.

It is a further aspect of the present invention to provide the method as described above, wherein step (A) and step (B) are successively performed.

It is a further aspect of the present invention to provide the method as described above, wherein the source gas reacts under conditions comprising a reaction temperature of 530° C. or lower and a reaction pressure of 30 MPa or lower in step (A).

It is a further aspect of the present invention to provide the method as described above, further comprising concentrating ammonia within the ammonia-containing gas obtained in step (A).

It is a further aspect of the present invention to provide the method as described above, further comprising recovering unreacted hydrogen and nitrogen after step (A) and recycling said unreacted hydrogen and nitrogen to step (A).

It is a further aspect of the present invention to provide the method as described above, wherein the recycling comprises performing dehydration treatment and/or drying treatment to remove water from said unreacted hydrogen and nitrogen.

It is a further aspect of the present invention to provide the method as described above, wherein ammonia water is produced using ammonia originating from the ammonia-containing gas obtained in step (A) and a microorganism able to produce an organic compound is cultured using the obtained ammonia water in step (B).

It is a further aspect of the present invention to provide the method as described above, wherein ammonia water is produced using ammonia originating from the ammonia-containing gas obtained in step (A), ammonia gas is recovered from the obtained ammonia water, and a microorganism able to produce an organic compound is cultured using said ammonia gas in step (B).

It is a further aspect of the present invention to provide the method as described above, wherein ammonia is used as a nitrogen source or a pH adjuster in step (B).

It is a further aspect of the present invention to provide the method as described above, wherein the microorganism is able to produce an organic compound selected from the group consisting of amino acids, organic acids, polysaccharides, proteins, antibiotics, and alcohols.

It is a further aspect of the present invention to provide the method as described above, wherein the microorganism is a bacterium or a fungus.

The present invention can provide a novel production system and a method of production for an organic compound or a microorganism that do not involve (or can minimize) the transport of liquid ammonia.

DESCRIPTION OF THE EXEMPLARY EMBODIMENTS

Figure 1:
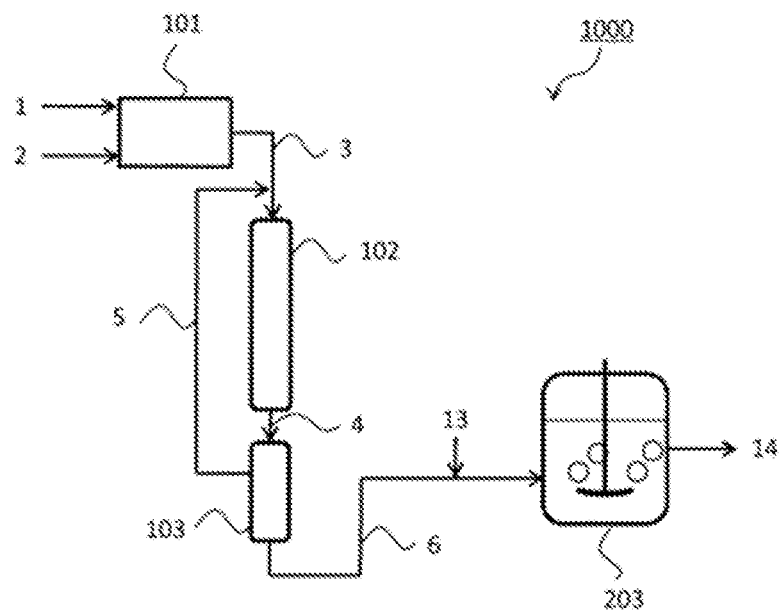
FIG. 1 is a schematic diagram (1) of a production system in one embodiment of the present invention.

The following describes the present invention in detail in conformity with exemplary embodiments thereof.

The present invention provides a novel production system for an organic compound or a microorganism.

As described above, ammonia synthesis by a large-scale production system assumes that the synthesized ammonia is liquefied, and then stored and transported in liquid form to ammonia consumption sites, and peripheral costs associated with the storage, transport and maintenance of liquid ammonia are increasing.

When ammonia is used as a nitrogen source or a pH adjuster in microbial fermentation, it is typically produced at the site where the microbial fermentation is performed, that is, produced on site. In this way, organic compounds or microorganisms can be produced by microbial fermentation without the storage and transport of liquid ammonia.

In one embodiment, the production system for an organic compound or a microorganism can include:

an ammonia synthesis apparatus that is configured to produce an ammonia-containing gas by reaction of a source gas containing hydrogen and nitrogen in the presence of a supported ruthenium catalyst; and a culture apparatus that is configured to culture a microorganism able to produce an organic compound using ammonia originating from the ammonia-containing gas obtained by using the ammonia synthesis apparatus.

<Ammonia Synthesis Apparatus>

In the ammonia synthesis apparatus of the production system, the source gas containing hydrogen and nitrogen is reacted in the presence of the ruthenium catalyst and a support to synthesize the ammonia-containing gas.

As described above, ammonia is currently produced mainly by the Haber-Bosch process. In the Haber-Bosch process, a source gas containing hydrogen and nitrogen reacts under high-temperature, high-pressure conditions at 400° C. to 600° C. and 20 MPa to 100 MPa using a doubly promoted iron catalyst to synthesize ammonia.

The production system as described herein uses the ruthenium catalyst as an ammonia synthesis catalyst. The ruthenium catalyst can exhibit higher ammonia synthesis activity even under low pressure conditions than the doubly promoted iron catalyst used in the Haber-Bosch process.

The support for the ruthenium catalyst is not limited to a particular support so long as it can support ruthenium and does not hinder the catalytic activity of ruthenium in the ammonia synthesis; any known support may be used. Examples of the support can include oxides such as silicon oxide (silica), zinc oxide, aluminum oxide (alumina), magnesium oxide (magnesia), indium oxide, calcium oxide, zirconium oxide (zirconia), titanium oxide (titania), boron oxide, hafnium oxide, barium oxide, cerium oxide (ceria), and zeolite; nitrides such as silicon nitride, aluminum nitride, boron nitride, and magnesium nitride; and active carbon. One support may be used alone, or two or more supports may be used in combination.

The ruthenium catalyst may contain one or more of the following elements: alkaline metals, alkaline earth metals, and rare earth metals as a promoter component.

In view of ammonia synthesis activity, the amount of ruthenium in the ruthenium catalyst can be 0.01 wt % or higher, 0.02 wt % or higher, 0.03 wt % or higher, 0.05 wt % or higher, 0.1 wt % or higher, 0.3 wt % or higher, 0.5 wt % or higher, or 1 wt % or higher when the support is 100 wt %. To lessen the sintering of ruthenium particles during the ammonia synthesis reaction so to retain the expected ammonia synthesis activity, the upper limit of the amount of ruthenium can be 30 wt % or lower, 20 wt % or lower, 15 wt % or lower, or 10 wt % or lower.

When the promoter component is used, the amount of the promoter component in the ruthenium catalyst is not limited to a particular amount, but can be 0.01 wt % to 1,000 wt % or 1 wt % to 800 wt % when ruthenium is 100 wt %, in view of ammonia synthesis activity.

The specific surface area of the ruthenium catalyst, which is not limited to a particular value, can be 0.1 $m^2/g$ to 1,000 $m^2/g$ or 0.5 $m^2/g$ to 800 $m^2/g$. The specific surface area of the ruthenium catalyst can be measured by a BET adsorption method, for example.

A method of preparation for the ruthenium catalyst on the support is not limited to a particular method; an appropriate method may be selected from known methods in accordance with the type of chosen support and the like. Examples of the method can include an impregnation process, a sol-gel process, CVD, and sputtering.

In the production system, the ammonia synthesis apparatus is not limited to a particular configuration so long as it is configured to react the source gas containing hydrogen and nitrogen in the presence of the ruthenium catalyst and support to synthesize ammonia gas, and the apparatus can include an inlet for the source gas containing hydrogen and nitrogen, a reaction unit in which the source gas reacts in the presence of the catalyst to synthesize the ammonia-containing gas, and an outlet for the produced ammonia-containing gas, for example.

In the reaction unit of the ammonia synthesis apparatus, hydrogen and nitrogen in the source gas directly react in accordance with a formula: $3H_2+N_2 \Leftrightarrow 2NH_3$ under the effect of the catalyst to synthesize ammonia.

In view of making ammonia synthesis at the ammonia consumption sites easy, the reaction temperature can be 600° C. or lower, 550° C. or lower, 530° C. or lower, 500° C. or lower, 450° C. or lower, or 400° C. or lower. In view of ammonia synthesis activity, the lower limit of the reaction temperature can be 100° C. or higher, 150° C. or higher, 200° C. or higher, 250° C. or higher, or 300° C. or higher.

In view of making ammonia synthesis at the ammonia consumption sites easy, the reaction pressure can be 30 MPa or lower, 25 MPa or lower, or 20 MPa or lower. The supported ruthenium catalyst can achieve excellent ammonia synthesis activity even when the reaction pressure is further lowered. The reaction pressure may be 15 MPa or lower, 10 MPa or lower, 5 MPa or lower, 4 MPa or lower, 3 MPa or lower, 2 MPa or lower, or 1 MPa or lower, for example. In view of the ammonia concentration at the outlet of the ammonia synthesis apparatus governed by chemical equilibrium in one preferred embodiment, the lower limit of the reaction pressure can be 10 kPa or higher, 50 kPa or higher, or 100 kPa or higher. The reaction pressure is a gauge pressure (the same applies to the following).

In the reaction unit of the ammonia synthesis apparatus, the reaction mode may be any of a batch reaction mode, a closed circulatory system reaction mode, and a flow system reaction mode; in view of practicality, the flow system reaction mode is preferred. Known reactor structures can be employed such as an internal heat exchange type for the purpose of retaining an ammonia synthesis reaction rate at a high level by controlling an increase in the temperature of a catalyst layer by reaction and increasing equilibrium ammonia concentration and a quencher type that supplies the source gas in a divided manner in a fluid flow direction.

In the reaction unit of the ammonia synthesis apparatus, one ruthenium catalyst may be used alone, or two or more ruthenium catalysts may be used in combination. Alternatively, two or more catalysts including the supported ruthenium catalyst and other ammonia synthesis catalysts may be used in combination. When two or more catalysts are used, in accordance with a reaction mode, the two or more catalysts may be used after mixing them with each other, the catalysts may be used by stacking so as to form separate layers by type, or the catalysts may be filled into separate reaction tubes so as to be filled into different reaction tubes by type and then used by combining the reaction tubes.

When the supported ruthenium catalyst is used, in obtaining expected ammonia synthesis activity, it is important to reduce the water content within the source gas. In view of the stability of the catalyst in particular, the water content within the source gas can be 100 ppm by volume or lower or 50 ppm by volume or lower. The lower limit of the water content can be lower and may be 0 ppm by volume. When the production system includes a recycle apparatus for unreacted hydrogen and nitrogen described below, it is important that the water content within the source gas is within the range including a water content within gas recovered by the recycle apparatus.

The molar ratio (hydrogen/nitrogen) between hydrogen and nitrogen within the source gas can be 1/2 to 5/1, 1/2 to 3/1, 1/2 to 2/1, or 4/5 to 6/5.

Hydrogen within the source gas used for ammonia synthesis can be prepared by commonly known methods such as 1) a method that transforms a hydrocarbon (coal, petroleum, natural gas, or biomass, for example) into gas containing CO and $H_2$ by a steam reforming reaction, a partial oxidation reaction, or a combination of these reactions and then performs a CO shift reaction and decarbonation processing, 2) a method that electrolyzes water, and 3) a method that decomposes water using a photocatalyst. Alternatively, hydrogen may be supplied from a hydrogen cylinder, including a hydrogen cylinder curdle, the same applies to the following, or a hydrogen tank, including a mobile tank such as a hydrogen self-loader, the same applies to the following. Nitrogen within the source gas used for ammonia synthesis may be prepared by separating nitrogen from air using a nitrogen separation membrane or a cryogenic separation method. Alternatively, when hydrogen is prepared utilizing the partial oxidation reaction of the hydrocarbon, nitrogen within air used as an oxygen source may be utilized. Alternatively, nitrogen may be supplied from a nitrogen cylinder, including a nitrogen cylinder curdle, the same applies to the following, or a nitrogen tank, including a mobile tank such as a nitrogen self-loader, the same applies to the following.

The source gas containing hydrogen and nitrogen can be prepared using a process that can be performed advantageously at the ammonia consumption sites.

In the production system, ammonia concentration within the ammonia-containing gas synthesized by the ammonia synthesis apparatus can be 0.5% by volume or higher, 2% by volume or higher, 4% by volume or higher, 6% by volume or higher, 8% by volume or higher, or 10% by volume or higher. The ammonia-containing gas synthesized by the ammonia synthesis apparatus mainly contains unreacted hydrogen and unreacted nitrogen apart from ammonia.

In the production system of, the ammonia synthesis capacity (ammonia-ton/day) of the ammonia synthesis apparatus, which varies by the amount of ammonia usage in the culture apparatus, can be 300 ton/day or less, 200 ton/day or less, 100 ton/day or less, 80 ton/day or less, 60 ton/day or less, or 50 ton/day or less. The lower limit of the ammonia synthesis capacity, which is not limited to a particular amount, can be normally 0.1 ton/day or more, 1 ton/day or more, 2 ton/day or more, or the like.

In the production system, microorganisms having organic compound productivity are cultured using ammonia originating from the ammonia-containing gas obtained by using the ammonia synthesis apparatus. In culture, ammonia is used as the nitrogen source or the pH adjuster.

The ammonia-containing gas obtained by using the ammonia synthesis apparatus may be 1) supplied to the culture apparatus directly after being cooled or 2) supplied to the culture apparatus as concentrated ammonia gas or liquid ammonia, or ammonia water as needed, after being concentrated, or 3) ammonia gas may be recovered from the obtained ammonia water, and the recovered ammonia gas may be supplied to the culture apparatus. In the 2) and 3) embodiments, using ammonia "originating from" the ammonia-containing gas obtained by using the ammonia synthesis apparatus is envisioned. Ammonia may also be supplied to the culture apparatus after being transformed into nitrogen-containing compounds originating from ammonia including ammonium salts such as ammonium sulfate, nitric acid, and nitrates. In such an embodiment, ammonia is used as a raw material of the nitrogen source or the pH adjuster. Such an embodiment is also included in the expression "ammonia is used as the nitrogen source or the pH adjuster".

Consequently, in one embodiment, the production system further includes a cooler that cools the ammonia-containing gas obtained by using the ammonia synthesis apparatus. The cooler is not limited to a particular cooler so long as it can cool the ammonia-containing gas to a certain temperature; any of known coolers, a coil type heat exchanger or a shell-and-tube type heat exchanger, for example, may be used. The cooled ammonia-containing gas may be supplied to the culture apparatus as it is or supplied to the culture apparatus after being stored in a storage tank.

In another embodiment, the production system further includes an ammonia concentration apparatus that concentrates the ammonia within the ammonia-containing gas obtained by using the ammonia synthesis apparatus. The ammonia concentration apparatus is not limited to a particular apparatus so long as it can concentrate the ammonia within the ammonia-containing gas; any known concentration apparatuses may be used. Examples of the ammonia concentration apparatus can include a pressurized cooling apparatus, a gas separation membrane apparatus, and a pressure swing adsorption (PSA) apparatus.

When the pressurized cooling apparatus is used as the ammonia concentration apparatus, the conditions of pressurized cooling are suitably set so as to liquefy the ammonia within the ammonia-containing gas. Pressure during the pressurized cooling, which varies by reaction pressure in the reaction unit of the ammonia synthesis apparatus and temperature during the pressurized cooling, can be 10 kPa or higher, 50 kPa or higher, 100 kPa or higher, 0.2 MPa or higher, 0.3 MPa or higher, 0.4 MPa or higher, or 0.5 MPa or higher. The temperature during the pressurized cooling, which varies by the pressure during the pressurized cooling, can be 50° C. or lower, 40° C. or lower, 30° C. or lower, 20° C. or lower, 10° C. or lower, 5° C. or lower, 0° C. or lower, −5° C. or lower, or −10° C. or lower. The lower limit of the temperature, which is not limited to a particular temperature, can be normally −35° C. or higher, −30° C. or higher, or the like. The pressurized cooling apparatus is not limited to a particular apparatus so long as it can perform pressurized cooling of the ammonia-containing gas obtained by using the ammonia synthesis apparatus on the conditions; any of known pressurized cooling apparatuses may be used. Liquid ammonia obtained by pressurized cooling of the ammonia-containing gas may be supplied to the culture apparatus as it is or supplied to the culture apparatus after being stored in a storage tank.

When the gas separation membrane apparatus is used as the ammonia concentration apparatus, a hydrogen gas separation membrane, a nitrogen gas separation membrane, or a combination of these membranes is suitably used. The ammonia-containing gas obtained by using the ammonia synthesis apparatus mainly contains ammonia, unreacted hydrogen, and unreacted nitrogen, and at least either the unreacted hydrogen or the unreacted nitrogen is separated by the gas separation membrane, whereby the ammonia can be concentrated. The hydrogen gas separation membrane and the nitrogen gas separation membrane are not limited to particular membranes so long as they can separate the unreacted hydrogen or nitrogen within the ammonia-containing gas obtained by using the ammonia synthesis apparatus; any known hydrogen gas separation membranes and nitrogen gas separation membranes may be used. Alternatively, an ammonia gas separation membrane that can selectively separate the ammonia within the ammonia-containing gas may be used. In concentrating ammonia using the gas separation membrane apparatus, conditions including temperature and pressure may be determined in accordance with the chosen gas separation membrane. Pressure, on a crude gas side, during gas separation can be 10 kPa or higher, 50 kPa or higher, 100 kPa or higher, 0.2 MPa or higher, 0.3 MPa or higher, 0.4 MPa or higher, or 0.5 MPa or higher, for example. The upper limit of the gas pressure, on the crude gas side, which is not limited to a particular pressure, is normally the reaction pressure in the reaction unit of the ammonia synthesis apparatus or lower. The concentrated ammonia gas obtained by the gas separation membrane apparatus may be supplied to the culture apparatus as it is or supplied to the culture apparatus after being stored in a storage tank.

The pressure swing adsorption (PSA) apparatus may be used as the ammonia concentration apparatus. The PSA apparatus uses an adsorbent exhibiting selective adsorbability for the ammonia within the ammonia-containing gas and controls the adsorption and desorption of the ammonia by pressure change to separate the ammonia from the other gases to concentrate the ammonia. The PSA apparatus is not limited to a particular apparatus so long as it can concentrate the ammonia within the ammonia-containing gas; any known PSA apparatuses may be used. The ammonia within the ammonia-containing gas may be concentrated using a PSA apparatus described in Japanese Patent No. 2634015, for example.

In the PSA apparatus, pressure ($P_{ad}$) when the ammonia is adsorbed to the adsorbent and pressure ($P_{de}$) when the ammonia is desorbed from the adsorbent can satisfy $P_{ad} > P_{de}$. In view of efficiently concentrating the ammonia within the ammonia-containing gas, $P_{ad}$ and $P_{de}$ can satisfy $P_{ad} - P_{de}$ 10 kPa, $P_{ad} - P_{de}$ 50 kPa, $P_{ad} - P_{de}$ 100 kPa, $P_{ad} - P_{de} > 0.2$ MPa, $P_{ad} - P_{de}$ 0.3 MPa, $P_{ad} - P_{de}$ 0.4 MPa, or $P_{ad} - P_{de}$ 0.5 MPa. The upper limit of the difference ($P_{ad}-P_{de}$) between $P_{ad}$ and $P_{de}$ is normally the reaction pressure in the reaction unit of the ammonia synthesis apparatus or lower. $P_{ad}$, which is not limited to a particular pressure so long as it satisfies $P_{ad}>P_{de}$, may be determined in accordance with the adsorbability of the adsorbent used and is normally the reaction pressure in the reaction unit of the ammonia synthesis apparatus or less. $P_{de}$, which is not limited to a particular pressure so long as it satisfies $P_{ad}>P_{de}$, may be determined in accordance with the adsorbability of the adsorbent used and is normally 1 MPa or lower, 0.5 MPa or lower, 0.2 MPa or lower, 100 kPa or lower, 50 kPa or lower, 10 kPa or lower, or 0 kPa or lower. Temperature during the gas separation may be determined in accordance with the specific specification of the PSA apparatus.

When the PSA apparatus is used as the ammonia concentration apparatus, the PSA apparatus suitably includes two or more adsorption towers. The PSA apparatus including two adsorption towers, a first adsorption tower and a second adsorption tower, for example, is operated so as to perform an ammonia desorption process in the second adsorption tower when an ammonia adsorption process is performed in the first adsorption tower and perform the ammonia adsorption process in the second adsorption tower when the ammonia desorption process is performed in the first adsorption tower, whereby the ammonia within the ammonia-containing gas can be continuously concentrated. The concentrated ammonia gas obtained by the PSA apparatus may be supplied to the culture apparatus as it is or supplied to the culture apparatus after being stored in a storage tank.

When the PSA apparatus is used as the ammonia concentration apparatus, ammonia concentration within the concentrated ammonia gas obtained by the ammonia concentration apparatus can be 10% by volume or higher, 30% by volume or higher, 50% by volume or higher. The upper limit of the ammonia concentration can be higher and may be 100% by volume. Consequently, the "concentrating" of ammonia is a concept that includes the isolation of the ammonia from the ammonia-containing gas.

The ammonia-containing gas obtained by using the ammonia synthesis apparatus may be further purified using an ammonia purification apparatus after the ammonia is concentrated by the ammonia concentration apparatus.

As described above, the ammonia-containing gas obtained by using the ammonia synthesis apparatus contains the unreacted hydrogen and the unreacted nitrogen. These unreacted hydrogen and nitrogen are recycled as sources of ammonia synthesis, whereby system efficiency can be improved. Consequently, in one embodiment, the production system further includes a recycle apparatus that recovers the unreacted hydrogen and nitrogen on the downstream side of the ammonia synthesis apparatus and recycles a recovered gas to the upstream side of the ammonia synthesis apparatus.

In the embodiment in which the ammonia-containing gas obtained by using the ammonia synthesis apparatus is supplied to the culture apparatus as it is after being cooled, the recycle apparatus may be provided in the culture apparatus. The details of the recycle apparatus will be described below with reference to the drawings.

In the embodiment in which the ammonia-containing gas obtained by using the ammonia synthesis apparatus is concentrated and supplied as the concentrated ammonia gas or liquid ammonia (or ammonia water as needed) to the culture apparatus, the unreacted hydrogen and nitrogen can be selectively recovered in the ammonia concentration apparatus, and the recycle apparatus may be provided in the ammonia concentration apparatus.

The recycle apparatus is not limited to a particular apparatus so long as it can recover the unreacted hydrogen and nitrogen and recycle the recovered gas containing hydrogen and nitrogen to the upstream side of the ammonia synthesis apparatus; any known recycle apparatuses may be used. The recycle apparatus may include a pipe for the recovered gas and a pump for transporting the recovered gas, for example.

When the recovered gas contains water, if the gas is recycled as it is, the catalytic ability of the supported ruthenium catalyst used in the ammonia synthesis apparatus may be affected. Consequently, in one embodiment, the recycle apparatus can include a dehydrator that removes the water within the recovered gas. The dehydrator is not limited to a particular dehydrator so long as it can reduce the water content within the recovered gas to a value that does not affect the catalytic ability of the supported ruthenium catalyst; any of known dehydrators may be used. Examples of the dehydrator can include an apparatus that cools the recovered gas to condense and remove the water. In view of further reducing the water content within the recovered gas, the recycle apparatus may use a drier and may include the drier in addition to the dehydrator or in place of the dehydrator. The drier is not limited to a particular drier so long as it has a function of further reducing the water content within the recovered gas; any known driers may be used. Examples of the drier can include an apparatus that brings the recovered gas into contact with a moisture absorbent to perform dehydration; examples of the moisture absorbent in this apparatus can include, but are not limited to, chemical moisture absorbents such as calcium chloride, diphosphorus pentaoxide, and copper sulfate anhydride; and physical moisture absorbents such as silica gel, alumina gel, and zeolite.

<Culture Apparatus>

In the production system, the culture apparatus cultures microorganisms having organic compound productivity using ammonia originating from the ammonia-containing gas obtained by using the ammonia synthesis apparatus.

Techniques for culturing microorganisms having organic compound productivity to produce organic compounds are widely known. The present invention can be applied widely to such microorganism fermentation techniques. Examples of the organic compounds produced in microorganism fermentation can include amino acids, organic acids, polysaccharides, proteins, antibiotics, and alcohols. Examples of the amino acids can include glycine, alanine, valine, leucine, isoleucine, serine, threonine, cysteine, cystine, methionine, phenylalanine, tyrosine, tryptophan, proline, hydroxyproline, asparagine, glutamine, aspartic acid, glutamic acid, lysine, histidine, and arginine. Examples of the organic acids can include acetic acid, lactic acid, pyruvic acid, succinic acid, malic acid, itaconic acid, citric acid, acrylic acid, propionic acid, and fumaric acid. Examples of the polysaccharides can include xanthan, dextran, alginate, hyaluronic acid, curdlan, gellan, scleroglucan, and pullulan. Examples of the proteins can include hormones, lymphokines, interferons, and enzymes, such as amylase, glucoamylase, invertase, lactase, protease, and lipase. Examples of the antibiotics can include antimicrobial agents, such as β-lactams, macrolides, ansamycin, tetracycline, chloramphenicol, peptidergic antibiotics, and aminoglycosides, antifungal agents, such as polyoxin B, griseofulvin, and polyenemacrolides, anticancer agents, daunomycin, adriamycin, dactinomycin, mithramycin, and bleomycin, protease/peptidase inhibitors, such as leupeptin, antipain, and pepstatin, and cholesterol biosynthesis inhibitors, such as compactin, lovastatin, and pravastatin. Examples of the alcohols can include ethanol, isopropanol, glycerin, propylene glycol, trimethylene glycol, 1-butanol, and sorbitol. Other examples of the organic compounds produced in microorganism fermentation can include acrylamide, diene compounds (such as isoprene), and pentanediamine.

The microorganisms having organic compound productivity can include both 1) microorganisms intrinsically having organic compound productivity and 2) microorganisms that have acquired organic compound productivity through the introduction of organic compound production genes by gene recombination although they do not have or do not substantially have organic compound productivity intrinsically. As to the microorganisms having organic compound productivity, various kinds of microorganisms are known in accordance with the type of organic compounds; these known microorganisms may be widely used. So long as ammonia can be used as the nitrogen source or the pH adjuster in culture, the present invention can be widely applied also to microorganisms to be developed in the future.

The microorganisms, which are not limited to particular microorganisms so long as they have organic compound productivity, are preferably bacteria or fungi. Examples of the bacteria can include the *Escherichia* bacteria, the *Pantoea* bacteria, the *Corynebacterium* bacteria, the *Enterobacter* bacteria, the *Clostridium* bacteria, the *Bacillus* bacteria, the *Lactobacillus* bacteria, the *Streptomyces* bacteria, the *Streptococcus* bacteria, and the *Pseudomonas* bacteria. Examples of the fungi can include the *Saccharomyces* fungi, the *Schizosaccharomyces* fungi, the *Yarrowia* fungi, the *Trichoderma* fungi, the *Aspergillus* fungi, the *Fusarium* fungi, and the *Mucor* fungi.

Examples of the *Escherichia* bacteria can include *Escherichia coli*. Examples of the *Pantoea* bacteria can include *Pantoea ananatis*. Examples of the *Corynebacterium* bacteria can include *Corynebacterium glutamicum* and *Corynebacterium ammoniagenes*. Examples of the *Enterobacter* bacteria can include *Enterobacter aerogenes*. Examples of the *Clostridium* bacteria can include *Clostridium acetobutylicum*. Examples of the *Bacillus* bacteria can include *Bacillus subtilis* and *Bacillus amyloliquefaciens*. Examples of the *Lactobacillus* bacteria can include *Lactobacillus yamanashiensis, Lactobacillus animalis, Lactobacillus hilgardii,* and *Lactobacillus brevis*. Examples of the *Streptomyces* bacteria can include *Streptomyces clavuligerus, Streptomyces venezuelae,* and *Streptomyces peucetius*. Examples of *Streptococcus* bacteria can include *Streptococcus equi* and *Streptococcus mutans*. Examples of the *Pseudomonas* bacteria can include *Pseudomonas fluorescens, Pseudomonas aeruginosa, Pseudomonas elodea,* and *Pseudomonas putida*. Examples of the *Saccharomyces* fungi can include *Saccharomyces cerevisiae*. Examples of the *Schizosaccharomyces* fungi can include *Schizosaccharomyces pombe*. Examples of the *Yarrowia* fungi can include *Yarrowia lipolytica*. Examples of the *Trichoderma* fungi can include *Trichoderma reesei*. Examples of the *Aspergillus* fungi can include Aspergullus *terreus* and *Aspergillus oryzae*. Examples of the *Fusarium* fungi can include *Fusarium hetereosporum*. Examples of the *Mucor* fungi can include Mucorjavanicus.

When the production system produces amino acids, examples of the microorganisms that can be suitably used can include the following: when the target substance is L-lysine, for example, examples thereof can include *Escherichia Coli* A J11442 (NRRL B-12185, FERM BP-1543) (refer to U.S. Pat. No. 4,346,170), *Brevibacterium lactofermentum* AJ3990 (ATCC31269) (refer to U.S. Pat. No. 4,066,501), and Lys-producing bacteria WC196LC/pCABD2 (WO 2010/061890). WC196ΔcadΔΔldc is a strain constructed by destroying the cadA and ldcC genes that code lysine decarboxylase from the WC196 strain. WC196ΔcadΔΔldc/pCABD2 is a strain constructed by introducing a plasmid pCABD2 (U.S. Pat. No. 6,040,160) containing a lysine biosynthetic gene to WC196ΔcadΔΔldc. WC196ΔcadΔΔldc was named AJ110692 and was deposited at International Patent Organism Depositary, National Institute of Advanced Industrial Science and Technology (currently Patent Microorganisms Depositary, National Institute of Technology and Evaluation, No. 120, 2-5-8 Kazusakamatari, Kisarazu-shi, Chiba 292-0818, Japan) with an accession number of FERM BP-11027 on Oct. 7, 2008. Examples thereof for L-threonine can include *Escherichia Coli* VKPM B-3996 (RIA 1867, VKPM B-3996) (refer to U.S. Pat. No. 5,175,107) and *Corynebacterium acetoacidophilum* AJ12318 (FERM BP-1172) (refer to U.S. Pat. No. 5,188,949); examples thereof for L-phenylalanine can include *Escherichia Coli* AJ12604 (FERM BP-3579) (refer to European Patent Application Laid-open No. 488,424), and *Brevibacterium lactofermentum* AJ12637 (FERM BP-4160) (refer to French Patent Application Laid-open No. 2,686,898); examples thereof for L-glutamic acid can include *Escherichia Coli* AJ12624 (FERM BP-3853) (refer to French Patent Application Laid-open No. 2,680,178) and *Brevibacterium lactofermentum* AJ12475 (FERM BP-2922) (refer to U.S. Pat. No. 5,272,067), and 2256ΔldhΔΔsucAyggB* prepared with *Corynebacterium glutamicum* ATCC13869 as a mother strain (WO 2014/185430); examples thereof for L-leucine can include *Escherichia Coli* AJ11478 (FERM P-5274) (refer to Japanese Examined Patent Application Publication No. S62-34397) and *Brevibacterium lactofermentum* AJ3718 (FERM P-2516) (refer to U.S. Pat. No. 3,970,519); examples thereof for L-isoleucine can include *Escherichia Coli* KX141 (VKPM B-4781) (refer to European Patent Application Laid-open No. 519,113) and *Brevibacterium flavum* AJ12149 (FERM BP-759) (refer to U.S. Pat. No. 4,656,135); and examples thereof for L-valine can include *Escherichia Coli* VL1970 (VKPM B-4411) (refer to European Patent Application Laid-open No. 519,113) and *Brevibacterium lactofermentum* AJ12341 (FERM BP-1763) (refer to U.S. Pat. No. 5,188,948).

When the production system produces organic acids, examples of the microorganisms that can be suitably used can include the following: when the target substance is L-lactic acid, for example, examples thereof can include *Lactobacillus yamanashiensis, Lactobacillus animalis,* and *Saccharomyces cerevisiae*; examples thereof for pyruvic acid can include *Escherichia Coli* and *Pseudomonas fluorescens*; examples thereof for succinic acid can include *Escherichia Coli* and *Pantoea ananatis*; examples thereof for itaconic acid can include *Aspergillus terreus*; and examples thereof for citric acid can include *Escherichia Coli* (refer to WO 2007/097260 and Japanese Patent Application Laid-open No. 2010-187542, for example).

When the production system produces polysaccharides, examples of the microorganisms that can be suitably used can include the following: when the target substance is dextran, for example, examples thereof can include *Lactobacillus hilgardii* and *Streptococcus mutans*; examples thereof for alginate can include *Pseudomonas aeruginosa*; examples thereof for hyaluronic acid can include *Streptococcus equi* and *Streptococcus mutans*; and examples thereof for gellan can include *Pseudomonas elodea* (refer to Japanese Patent Application Laid-open No. 2011-116825 and Japanese Patent Application Laid-open No. 2007-9092, for example).

When the production system produces proteins, examples of the microorganisms that can be suitably used can include the following: when the target substance is any of various kinds of hormones or interferons, for example, examples thereof can include *Saccharomyces cerevisiae*; examples thereof for amylase, glucoamylase, protease, or lipase can include *Bacillus subtilis* and *Aspergillus oryzae*; and examples thereof for invertase or lactase can include *Saccharomyces cerevisiae* and *Aspergillus oryzae* (refer to WO 2006/67511 and Japanese Patent Application Laid-open No. 2003-153696, for example).

When the production system produces antibiotics, examples of the microorganisms that can be suitably used can include the following: when the target substance is a β-lactam such as penicillin, for example, examples thereof can include *Pseudomonas putida* and *Streptomyces clavuligerus*; examples thereof for macrolides such as erythromycin and azithromycin can include *Streptomyces venezuelae*; examples thereof for daunomycin can include *Streptomyces peucetius*; examples thereof for pravastatin can include *Streptomyces clavuligerus* (refer to WO 96/10084, Japanese Patent Application Laid-open No. 2002-53589, WO 2005/54265, and WO 2007/147827, for example).

When the production system produces alcohols, examples of the microorganisms that can be used can include the following: when the target substance is ethanol, for example, examples thereof can include *Saccharomyces cerevisiae, Schizosaccharomyces pombe*, and *Lactobacillus brevis*; and examples thereof for trimethylene glycol can include *Escherichia coli* (refer to WO 2007/97260, for example).

A medium for culturing microorganisms can contain a carbon source and a nitrogen source for being converted into organic compounds. Examples of the carbon source can include carbohydrates such as monosaccharides, disaccharides, oligosaccharides, and polysaccharides; invert sugars obtained by hydrolyzing sucrose; glycerol; $C_1$ compounds such as methanol, formaldehyde, formates, carbon monoxide, and carbon dioxide; oils such as corn oil, palm oil, and soybean oil; acetates; animal fats; animal oils; fatty acids such as saturated fatty acids and unsaturated fatty acids; lipids; phospholipids; glycerolipids; glycerin fatty acid esters such as monoglycerides, diglycerides, and triglycerides; polypeptides such as microbial proteins and vegetable proteins; renewable carbon sources such as a hydrolyzed biomass carbon source; yeast extracts; and combinations thereof. Examples of the nitrogen source can include inorganic nitrogen sources such as ammonia, ammonium salts, nitric acid, and nitrates; organic nitrogen sources such as urea, amino acids, and proteins; and combinations thereof. The medium can contain inorganic ions and other organic minor components as needed in addition to the carbon source and the nitrogen source. The inorganic ions and the other organic minor components may be any known components. The medium may be a natural medium or a synthetic medium.

Culture conditions are not limited to particular conditions so long as the conditions can produce a target organic compound; any standard microorganism culture conditions may be used. The culture temperature can be 20° C. to 37° C. In accordance with the characteristics of the microorganism, culture can be performed under an aerobic, anoxic, or anaerobic condition.

As to the method of culture, known methods such as a batch culture method, a fed-batch culture method, and a continuous culture method may be used.

A liquid depth, that is, the medium depth, in the culture apparatus may be determined as appropriate in accordance with the characteristics of the microorganism. When the medium is required to be static for microbial growth in aerobic culture, for example, a culture apparatus, such as a culture tank, having a small liquid depth may be used. When oxygen demand is large, a submerged culture apparatus may be used, in which air is directly passed through an agitation tank or a bubble tower to supply oxygen to the medium.

A method for supplying ammonia to the culture apparatus is not limited to a particular method; in accordance with the form of ammonia, such as ammonia gas, liquid ammonia, or ammonia water, ammonia may be supplied to the vapor phase of the culture apparatus or supplied into the medium. When ammonia is supplied to the culture apparatus after being transformed into the nitrogen-containing compounds originating from ammonia, such as ammonium salts, urea, nitric acid, or nitrates, ammonia may be supplied into the medium. The supply of ammonia or the nitrogen-containing compound originating from ammonia can be performed in accordance with a known method. The supply amount of ammonia or the nitrogen-containing compound originating from ammonia to the culture apparatus may be determined in accordance with the specific design of the culture apparatus including the type of the microorganism having organic compound productivity.

The following describes embodiments of the production system with reference to the accompanying drawings.

FIG. 1 illustrates a production system 1000 including a source gas production apparatus 101, an ammonia synthesis apparatus 102, an ammonia concentration apparatus 103 selected from a pressurized cooling apparatus and a PSA apparatus, and a culture apparatus 203.

In the production system 1000, first, a hydrogen source gas 1 and air 2 are supplied to the source gas production apparatus 101. The hydrogen source gas 1 may be a hydrocarbon (coal, petroleum, natural gas, or biomass, for example) or water in accordance with a hydrogen production process in the source gas production apparatus 101. Examples of the hydrogen production process can include, as described above, 1) a method that transforms a hydrocarbon into gas containing CO and $H_2$ by a steam reforming reaction, a partial oxidation reaction, or a combination of these reactions and then performs a CO shift reaction and decarbonation processing, 2) a method that electrolyzes water, and 3) a method that decomposes water using a photocatalyst. The source gas production apparatus 101 also produces nitrogen. Nitrogen may be prepared by separating nitrogen from air using a nitrogen separation membrane or a cryogenic separation method. Alternatively, when hydrogen is prepared utilizing the partial oxidation reaction of the hydrocarbon, nitrogen within air used as an oxygen source may be used.

A source gas 3 containing hydrogen and nitrogen produced by the source gas production apparatus 101 is supplied to the ammonia synthesis apparatus 102. In the ammonia synthesis apparatus 102, the source gas containing hydrogen and nitrogen reacts in the presence of the supported ruthenium catalyst to synthesize the ammonia-containing gas.

A synthesized ammonia-containing gas 4 is supplied to the ammonia concentration apparatus 103 selected from the pressurized cooling apparatus and the PSA apparatus. When the ammonia concentration apparatus 103 is the pressurized cooling apparatus, liquid ammonia 6 is obtained. When the ammonia concentration apparatus 103 is the PSA apparatus, concentrated ammonia gas 6 is obtained. The obtained liquid ammonia or concentrated ammonia gas may be stored in a storage tank (not illustrated).

The obtained liquid ammonia or concentrated ammonia gas 6 is supplied to the culture apparatus 203. An appropriate medium in accordance with the type of the microorganisms having organic compound productivity is introduced to the culture apparatus 203, and air 13 is supplied thereto as needed. In the culture apparatus 203, the ammonia 6 is used as the nitrogen source or the pH adjuster. The microorganisms having organic compound productivity is cultured, whereby an organic compound or a microorganism 14 can be produced.

The production system 1000 illustrated in FIG. 1 includes a recycle apparatus (not illustrated) that recovers unreacted hydrogen and nitrogen separated by the ammonia concentration apparatus 103 and recycles recovered gas 5 to the upstream side of the ammonia synthesis apparatus 102.

Figure 2:
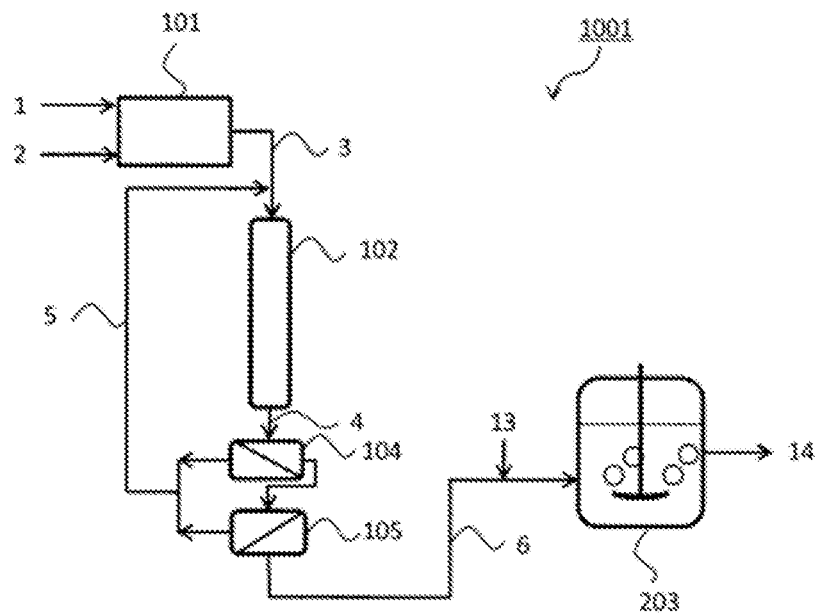
FIG. 2 is a schematic diagram (2) of a production system in one embodiment of the present invention.

FIG. 2 illustrates a production system 1001 including the source gas production apparatus 101, the ammonia synthesis apparatus 102, gas separation membrane apparatuses (ammonia concentration apparatuses) 104 and 105, and the culture apparatus 203. In the production system 1001, the source gas production apparatus 101, the ammonia synthesis apparatus 102, and the culture apparatus 203 are as described above.

The production system 1001 includes the gas separation membrane apparatuses 104 and 105 as the ammonia concentration apparatus. A hydrogen gas separation membrane 104 and a nitrogen gas separation membrane 105 can be used in combination, for example. The production system 1001 including the gas separation membrane apparatuses 104 and 105 can obtain the concentrated ammonia gas 6. The obtained concentrated ammonia gas may be stored in a storage tank (not illustrated).

The production system 1001 illustrated in FIG. 2 includes a recycle apparatus that recovers unreacted hydrogen and nitrogen separated by the gas separation membrane apparatuses 104 and 105 and recycles the recovered gas 5 to the upstream side of the ammonia synthesis apparatus 102.

Figure 3:
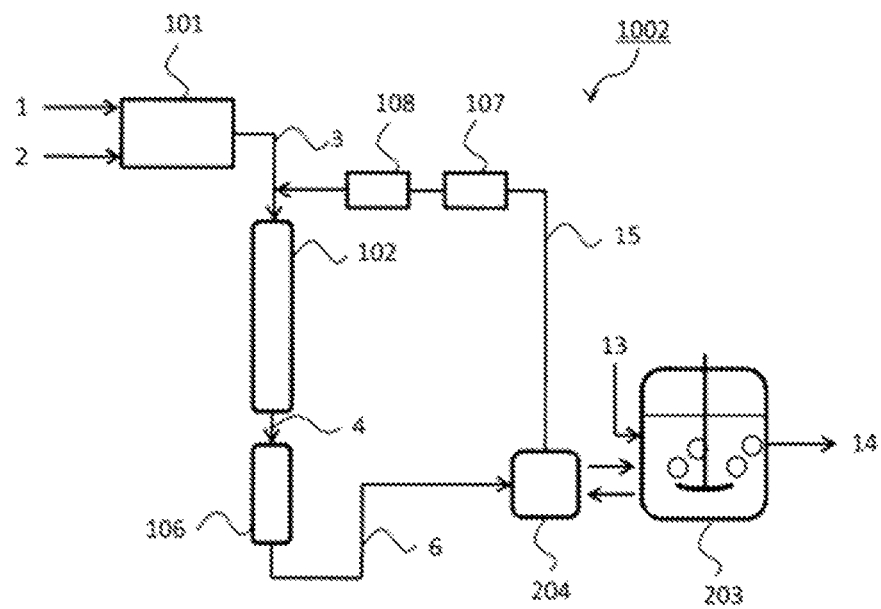
FIG. 3 is a schematic diagram (3) of a production system in one embodiment of the present invention.

FIG. 3 illustrates a production system 1002 including the source gas production apparatus 101, the ammonia synthesis apparatus 102, a cooler 106, and the culture apparatus 203. In the production system 1002, the source gas production apparatus 101 and the ammonia synthesis apparatus 102 are as described above.

In the production system 1002, the ammonia-containing gas 4 obtained by using the ammonia synthesis apparatus 102 is cooled by the cooler 106. Next, the cooled ammonia-containing gas 6 is supplied to a premixer 204 provided in the culture apparatus 203.

In the production system 1002, the culture apparatus 203 includes the premixer 204. Between the premixer 204 and the culture tank of the culture apparatus 203, the medium circulates. In the premixer 204, ammonia is premixed with the circulating medium. With this premixing, the medium mixed with ammonia is supplied to the culture tank of the culture apparatus 203.

The cooled ammonia-containing gas 6 contains unreacted hydrogen and nitrogen. The production system 1002 includes a recycle apparatus that recovers the unreacted hydrogen and nitrogen in the premixer 204 and recycles recovered gas 15 to the upstream side of the ammonia synthesis apparatus 102. The recovered gas 15 contains water originating from the medium. In the production system 1002, the recycle apparatus includes a dehydrator 107 that removes the water in the recovered gas 15. The production system 1002 also includes a drier 108 that further dries the recovered gas 15.

Figure 4:
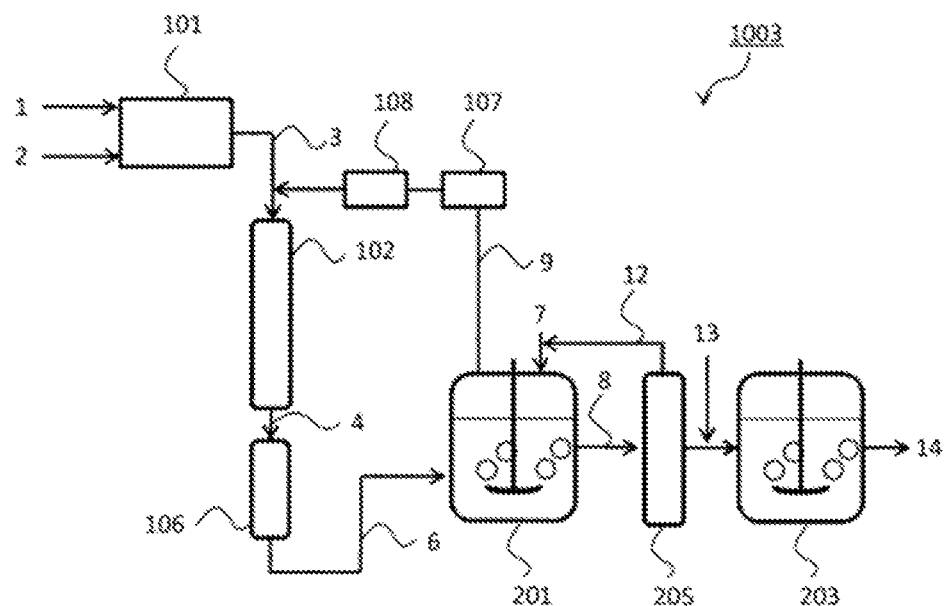
FIG. 4 is a schematic diagram (4) of a production system in one embodiment of the present invention.

FIG. 4 illustrates a production system 1003 including the source gas production apparatus 101, the ammonia synthesis apparatus 102, the cooler 106, the ammonia water production apparatus 201, an ammonia stripping apparatus 205, and the culture apparatus 203. In the production system 1003, the source gas production apparatus 101, the ammonia synthesis apparatus 102, the cooler 106, and the culture apparatus 203 are as described above.

In the production system 1003, the ammonia-containing gas 4 obtained by using the ammonia synthesis apparatus 102 is cooled by the cooler 106. Next, the cooled ammonia-containing gas 6 is supplied to the ammonia water production apparatus 201. Water 7 is also supplied to the ammonia water production apparatus 201. The ammonia water production apparatus dissolves ammonia within the cooled ammonia-containing gas 6 in the water 7 and can thereby produce ammonia water 8. The method and conditions of dissolution are not limited to particular ones so long as they can produce ammonia water with an expected concentration; any of known methods and conditions may be used.

The cooled ammonia-containing gas 6 contains unreacted hydrogen and nitrogen. The production system 1003 includes a recycle apparatus that recovers the unreacted hydrogen and nitrogen in the ammonia water production apparatus 201 and recycles a recovered gas 9 to the upstream side of the ammonia synthesis apparatus 102. The recovered gas 9 contains water originating from the water 7 used in the ammonia water production apparatus 201. In the production system 1003, the recycle apparatus includes a dehydrator 107 that removes the water within the recovered gas 9. The production system 1003 also includes a drier 108 that further dries the recovered gas 9.

In the production system 1003, the produced ammonia water 8 is used further for the production of the organic compound or the microorganism. Specifically, the produced ammonia water 8 is supplied to the ammonia stripping apparatus 205 to recover ammonia gas from the ammonia water. The ammonia stripping apparatus 205 is not limited to a particular apparatus so long as it can recover the ammonia gas from the ammonia water; any of known stripping apparatuses may be used. The ammonia recovered by the ammonia stripping apparatus 205 is used as the nitrogen source or the pH adjuster, and the microorganism having organic compound productivity is cultured in the culture apparatus 203, whereby the organic compound or the microorganisms 14 can be produced. Water 12 removed by the ammonia stripping apparatus 205 may be merged with the water 7 as illustrated in FIG. 4 or discharged.

The production system 1003 can also transport the ammonia water 8 produced by the ammonia water production apparatus 201 and produce the organic compound or the microorganism at geographically remote sites.

The production systems for an organic compound or a microorganism are described with reference to FIG. 1 to FIG. 4. Although ammonia is supplied to the culture apparatus 203 as the nitrogen source or the pH adjuster in the embodiments illustrated in FIG. 1 to FIG. 4, the ammonia may be transformed into any of other nitrogen-containing compounds (ammonium salts, urea, nitric acid, or nitrates), and the nitrogen-containing compound may be then supplied to the culture apparatus 203. Such a modification is also included in the scope of the present invention. In the production systems illustrated in FIG. 1 to FIG. 4, a hydrogen supply apparatus such as a hydrogen cylinder or a hydrogen tank and a nitrogen supply apparatus such as a nitrogen cylinder or a nitrogen tank may be used in place of the source gas production apparatus 101. In the production systems illustrated in FIG. 1 to FIG. 3, the concentrated ammonia 6 such as the liquid ammonia or the concentrated ammonia gas is also suitably supplied to the culture apparatus 203 after being converted into ammonia water.

Method of Production

The present invention also provides a novel method of production for an organic compound or a microorganism. The method of production does not involve (or minimizes) the transport of liquid ammonia.

In one embodiment, the method of production for an organic compound or a microorganism can include:

(A) synthesizing an ammonia-containing gas by reaction of a source gas containing hydrogen and nitrogen in the presence of a supported ruthenium catalyst; and (B) culturing a microorganism having organic compound productivity using ammonia originating from the obtained ammonia-containing gas.

The supported ruthenium catalyst, the source gas, the ammonia-containing gas used in step (A) and conditions, such as temperature, pressure, and the like, when the ammonia-containing gas is synthesized are as described in the section here entitled "Production System". An organic compound or a microorganism produced in step (B) and the method of production for the same are as described in the section herein entitled "Production System". The advantageous effects described for the production system are also applied to the method of production similarly.

In the method of production, step (A) and step (B) are successively performed. The phrase "step (A) and step (B) are successively performed" can mean that the ammonia-containing gas synthesized in step (A) is subjected to step (B) without being transported as liquid ammonia. The phrase "being transported as liquid ammonia" can mean transport between two geographically remote sites by pipeline, air, ship, automobile, and the like and does not include transport within a production site of an organic compound or a microorganism.

The method of production may further include a process of producing the source gas containing hydrogen and nitrogen from the hydrogen source gas and air. The methods of production for the hydrogen source gas and the source gas are as described in the section herein entitled "Production System.

The method of production may further include a process of concentrating the ammonia within the ammonia-containing gas obtained in step (A). The method for concentrating the ammonia within the ammonia-containing gas is as described in the section herein entitled "Production System".

The method of production may further include a step, hereinafter, referred to as step (C), of recovering unreacted hydrogen and nitrogen and recycling a recovered gas to step (A). In one embodiment, step (C) may include dehydration treatment and/or drying treatment removing water within the recovered gas. The methods of dehydration treatment and the drying treatment are as described in the section herein entitled "Production System".

One preferred embodiment of the method of production produces ammonia water using ammonia originating from the ammonia-containing gas obtained in step (A) and cultures a microorganism having organic compound productivity using the obtained ammonia water in step (B).

Another preferred embodiment of the method of production produces ammonia water using ammonia originating from the ammonia-containing gas obtained in step (A), recovers ammonia gas from the obtained ammonia water, and cultures a microorganism having organic compound productivity using the recovered ammonia gas in step (B).

The method of production may further include collecting a metabolite from a medium liquid after the end of culture. The method for collecting the metabolite is not limited to a particular method; the metabolite can be collected by combining an ion exchange resin method, a precipitation method, and other methods that have been conventionally commonly known.

EXAMPLES

Reference Example 1

<Synthesis of Cs—MgO Supporting Ru>

MgO (manufactured by Ube Material Industries, Ltd., Product No.: UC95) (1 g) was evacuated and heated at 500° C. for 5 hours and was immersed in a tetrahydrofuran solution dissolving $Ru_3(CO)_{12}$ in an Ar atmosphere. After the mixture was stirred for 3 hours, the solvent was removed by a rotary evaporator, and evacuation and heating were performed at 350° C. for 2 hours. With this procedure, a MgO catalyst supporting 2 wt % of Ru metal particles was obtained. Further, the obtained catalyst was immersed in an ethanol solution dissolving $Cs_2CO_3$ in an Ar atmosphere. In this process, the amount of $Cs_2CO_3$ was adjusted so as to give an element ratio between Cs and Ru of 1:1. After the mixture was stirred for 3 hours, the solvent was removed by a rotary evaporator, and evacuation treatment was performed at room temperature for 12 hours to obtain a Cs—MgO catalyst (powder) supporting 2 wt % of Ru metal particles. The BET specific surface area of the obtained catalyst was 12 m²/g. The Ru dispersion (%) measured by a CO adsorption method was 25.

<Ammonia Synthesis Reaction>

A synthesis reaction in which nitrogen gas ($N_2$) and hydrogen gas ($H_2$) react to produce ammonia gas ($NH_3$) was performed. The catalyst obtained by the above method in an amount of 0.1 g was charged into a glass tube, and the synthesis reaction was performed by a fixed bed flow reactor. The gas flows were set to $N_2$: 15 mL/min and $H_2$: 45 mL/min giving a total of 60 mL/min, and the reaction was performed at a reaction temperature of 340° C. and a pressure of atmospheric pressure. The gas that had emerged from the flow reactor was bubbled in a 0.005 M aqueous sulfuric acid solution to dissolve the produced ammonia in the solution, and the produced ammonium ions were quantified by an ion chromatograph.

The 2 wt % Ru/Cs—MgO catalyst (Cs/Ru element ratio=1) showed an ammonia production rate of 2,367 $\mu mol g^{-1} h^{-1}$ at 340° C. The TOF ($\times 10^{-3}$ s$^{-1}$) was 13.3.

Reference Example 2

<Synthesis of Ru—Cs/MgO Catalyst (Catalyst Supporting Cs Together with Ru on MgO)>

MgO (manufactured by Ube Material Industries, Ltd., Product No.: UC95) powder was put into a quartz glass container and was evacuated at 500° C. for 6 hours to perform dehydration treatment thereon. The dehydrated MgO in an amount of 1.00 g was put into 60 mL of a super dehydrated THF solvent (manufactured by Wako Pure Chemical Industries, Ltd., Product No.: 207-17765). $Ru_3(CO)_{12}$ (purity: 99%, manufactured by Aldrich, Product No.: 245011) in an amount of 0.02 g was put into the solvent so as to give a Ru support amount of 6 wt % relative to a Ru—Cs/MgO catalyst, and the mixture was stirred at room temperature for 4 hours to support Ru metal on MgO in an impregnated manner. Using an evaporator, the sample was dried and solidified at 40° C. and 16.0 kPa for 7 hours (1.01 g). The dried and solidified sample in an amount of 0.81 g was put into 100 mL of dehydrated ethanol. $Cs_2CO_3$ (manufactured by Kanto Chemical Co., Inc., Product No.: 07184-33) in an amount of 0.078 g was put thereinto so as to give a molar ratio between Ru and Cs of 1:1, and the mixture was stirred at room temperature for 4 hours to support Cs metal on Ru/MgO in an impregnated manner. Using an evaporator, the sample was dried and solidified at room temperature and 9.0 kPa for 7 hours. A 6 wt % Ru—Cs/MgO catalyst in an amount of 0.087 g was obtained.

<Production of Ammonia Water>

A reaction in which nitrogen gas ($N_2$) and hydrogen gas ($H_2$) react to produce ammonia gas ($NH_3$) was performed. The obtained catalyst in an amount of 0.2 g was charged into a pressure-resistant tube, and the reaction was performed by a fixed bed flow reactor. The gas flows were set to $N_2$: 15 mL/min and $H_2$: 45 mL/min giving a total of 60 mL/min, and the reaction was performed at a pressure of 0.9 MPa and a reaction temperature of 400° C. The gas that had emerged from the flow reactor was passed through water cooled at about 3° C.; the production rate of ammonia was 3,734 $\mu mol g^{-1} h^{-1}$. The produced $NH_3$ was dissolved in the water to obtain Aqueous Ammonia 1 (liquid amount: 200 g, $N_{H4}^+$ amount: 1.60 g) was obtained in about 109 hours.

Reference Example 3

<Production of Ammonium Sulfate Solution>

In the production of ammonia water in Reference Example 2, at a reaction temperature of 400° C., the reaction pressure was changed from 0.9 MPa to 0.1 MPa, and besides, passing the gas that had emerged from the circulation reactor through the water cooled at about 3° C. was changed to passing the gas that had emerged from the flow reactor through a 0.220 M aqueous sulfuric acid solution at room temperature. Ammonium sulfate was produced similarly to Reference Example 2 except the above matters. The production rate of ammonia was 3,531 $\mu mol h^{-1} g^{-1}$. Ammonium Sulfate Solution 1 (liquid amount: 100 g, $NH_4^+$ amount: 0.81 g) was obtained in about 56 hours.

Example 1

The ammonia gas synthesized in Reference Example 1 was dissolved in water to obtain ammonia water.

Ammonia gas was recovered from the obtained ammonia water using an ammonia stripping apparatus, and using the ammonia gas, *E. coli* MG1655 was cultured.

From a growing curve, the ammonia gas obtained was revealed to be able to be used for fermentation and culture production.

Example 2

Using Aqueous Ammonia 1 produced in Reference Example 2 and *E. coli*, the production culture of L-lysine was performed. The following media were used for the culture.

LB Agar Medium:

tryptone: 10 g/L, yeast extract: 5 g/L, NaCl: 10 g/L, agar: 15 g/L

Lys Ammoniacal Liquor Medium:

glucose: 20 g/L, $NH_3$: 3.09 g/L (Aqueous Ammonia 1 produced in Reference Example 2 was used), $MgSO_4 \cdot 7H_2O$: 1 g/L, $KH_2PO_4$: 1 g/L, yeast extract: 2 g/L, $FeSO_4 \cdot 7H_2O$: 0.01 g/L, $MnSO_4 \cdot 5H_2O$: 0.008 g/L, adjusted to have a pH of 7.0 using $H_2SO_4$ Lys-producing bacteria WC196ΔcadΔΔldc/pCABD2 were cultured in the LB agar medium with streptomycin added so as to have a final concentration of 80 mg/L at 37° C. for an entire day and night. All the bacteria on the plate with a diameter of 90 mm were scraped together from the cultured agar medium and were suspended in 3 mL of a physiological saline solution to prepare a bacteria solution.

The bacteria solution was planted to a thick test tube charged with 5 mL of the Lys ammoniacal liquor medium to which streptomycin had been added so as to have a final concentration of 80 mg/L and calcium carbonate dry-sterilized in advance had been added so as to have a final concentration of 30 g/L so as to have an absorbance at a wavelength of 620 nm (O.D. 620 nm) of 0.126, and shake culture was performed at 37° C. and 120 rpm for 24 hours.

Example 3

In Example 2, the Lys ammoniacal liquor medium was changed to the following Lys ammonium sulfate medium. The production culture of L-lysine was performed similarly to Example 2 except the above matter.

Lys Ammonium Sulfate Medium:

glucose: 20 g/L, $(NH_4)_2SO_4$: 12 g/L (Ammonium Sulfate Solution 1 produced in Reference Example 3 was used), $MgSO_4 \cdot 7H_2O$: 1 g/L, $KH_2PO_4$: 1 g/L, yeast extract: 2 g/L, $FeSO_4 \cdot 7H_2O$: 0.01 g/L, $MnSO_4 \cdot 5H_2O$: 0.008 g/L, adjusted to have a pH of 7.0 using KOH Comparative Example 1

In Example 2, Aqueous Ammonia 1 in the Lys ammoniacal liquor medium was changed to commercially available aqueous ammonia (manufactured by Junsei Chemical Co., Ltd., Product No.: 13370-0301). The production culture of L-lysine was performed similarly to Example 2 except the above matter.

Comparative Example 2

In Example 3, Ammonium Sulfate Solution 1 in the Lys ammonium sulfate medium was changed to a commercially available ammonia sulfate solution (manufactured by Junsei Chemical Co., Ltd., Product No.: 83110-0367). The production culture of L-lysine was performed similarly to Example 3 except the above matter.

TABLE 1

| | Nitrogen source | O.D.620 nm (xl) | Production amount of L-lysine (g/L) | Yeild (%) |
|---|---|---|---|---|
| Example 2 | Aqueous Ammonia 1 | 8.31 ± 0.05 | 8.3 ± 0.0 | 39.6 ± 0.2 |
| Example 3 | Ammonium Sulfate Solution 1 | 9.95 ± 0.10 | 8.4 ± 0.0 | 39.5 ± 0.2 |
| Comparative Example 1 | Aqueous Ammonia (commercially available product) | 8.45 ± 0.13 | 8.4 ± 0.1 | 39.5 ± 0.3 |
| Comparative Example 2 | Ammonium Sulfate Solution (commercially available product) | 10.22 ± 0.06 | 8.7 ± 0.1 | 40.2 ± 0.3 |

The culture results are listed in the above table. Also when Aqueous Ammonia 1 produced in Reference Example 2 or Ammonium Sulfate Solution 1 produced in Reference Example 3 was used, bacterial growth and the production of L-lysine substantially equal to those of the examples cultured using the commercially available aqueous ammonia (Comparative Example 1) or the commercially available ammonium sulfate solution (Comparative Example 2) were revealed, showing that the ammonia gas can be used for fermentation and culture production.

Example 4

Using Aqueous Ammonia produced in Reference Example 2 and *Corynebacterium glutamicum*, the production culture of L-glutamic acid was performed. The following media were used for the culture.

CM-Ace Agar Medium:
glucose: 2.5 g/L, fructose: 2.5 g/L, sodium gluconate: 4 g/L, sodium succinate.6H$_2$O: 2 g/L, peptone: 10 g/L, yeast extract: 10 g/L, KH$_2$PO$_4$: 1 g/L, MgSO$_4$.7H$_2$O: 0.4 g/L, FeSO$_4$.7H$_2$O: 0.01 g/L, MnSO$_4$.5H$_2$O: 0.01 g/L, urea: 4 g/L, bean filtrate (soybean hydrolysate): 1.2 g/L (T-N), biotin: 1 mg/L, vitamin B1: 5 mg/L, adjusted to have a pH of 7.5 using KOH Glu Ammoniacal Liquor Medium:
glucose: 40 g/L, NH$_3$ (Aqueous Ammonia 1 produced in Reference Example 2 was used): 3.86 g/L, KH$_2$PO$_4$: 1 g/L, MgSO$_4$.7H$_2$O: 0.4 g/L, FeSO$_4$.7H$_2$O: 0.01 g/L, MnSO$_4$.5H$_2$O: 0.01 g/L, vitamin B1: 200 µg/L, biotin: 300 µg/L, bean filtrate: 0.48 g/L (T-N), K$_2$SO$_4$: 19.78 g/L, adjusted to have a pH of 8.0 using H$_2$SO$_4$ Glu producing bacteria 2256ΔldhΔΔsucAyggB* of *Corynebacterium glutamicum* were cultured in the CM-Ace agar medium at 31.5° C. for an entire day and night. The bacteria corresponding to 1/24 plate were scraped from the agar medium after culture and were planted to a thick test tube charged with 5 mL of the Glu ammoniacal liquor medium to which calcium carbonate dry-sterilized in advance had been added so as to have a final concentration of 30 g/L, and shake culture was performed at 31.5° C. and 120 rpm for 24 hours.

Example 5

In Example 4, the Glu ammoniacal liquor medium was changed to the following Glu ammonia sulfate medium. The production culture of L-glutamic acid was performed similarly to Example 4 except the above matter.

Glu Ammonium Sulfate Medium:
glucose: 40 g/L, (NH$_4$)$_2$SO$_4$: 15 g/L (Ammonium Sulfate Solution 1 produced in Reference Example 3 was used), KH$_2$PO$_4$: 1 g/L, MgSO$_4$.7H$_2$O: 0.4 g/L, FeSO$_4$.7H$_2$O: 0.01 g/L, MnSO$_4$.5H$_2$O: 0.01 g/L, vitamin B1: 200 µg/L, biotin: 300 µg/L, bean filtrate: 0.48 g/L (T-N), adjusted to have a pH of 8.0 using KOH.

Comparative Example 3

In Example 4, Aqueous Ammonia 1 in the Glu ammoniacal liquor medium was changed to commercially available aqueous ammonia (manufactured by Junsei Chemical Co., Ltd., Product No.: 13370-0301) The production culture of L-glutamic acid was performed similarly to Example 4 except the above matter.

Comparative Example 4

In Example 5, Ammonium Sulfate Solution 1 in the Glu ammonium sulfate medium was changed to a commercially available ammonium sulfate solution (manufactured by Junsei Chemical Co., Ltd., Product No.: 83110-0367). The production culture of L-glutamic acid was performed similarly to Example 5 except the above matter.

TABLE 2

| | Nitrogen source | O.D.620 nm (xl) | Production amount of L-glutamic acid (g/L) | Yield (%) |
|---|---|---|---|---|
| Example 4 | Aqueous Ammonia 1 | 31.93 ± 0.54 | 20.4 ± 0.0 | 51.8 ± 0.0 |
| Example 5 | Ammonium Sulfate Solution 1 | 27.57 ± 0.48 | 20.8 ± 0.1 | 50.2 ± 0.1 |
| Comparative Example 3 | Aqueous Ammonia (commercially available product) | 33.59 ± 0.56 | 20.8 ± 0.2 | 48.6 ± 0.5 |
| Comparative Example 4 | Ammonium Sulfate Solution (commercially available product) | 29.65 ± 0.68 | 21.8 ± 0.0 | 51.2 ± 0.0 |

The culture results are listed in the above table. Also when Aqueous Ammonia 1 produced in Reference Example 2 or Ammonium Sulfate Solution 1 produced in Reference Example 3 was used, bacterial growth and the production of L-glutamic acid substantially equal to those of the examples cultured using the commercially available aqueous ammonia (Comparative Example 3) or the commercially available ammonium sulfate solution (Comparative Example 4) were revealed, showing that the ammonia gas obtained can be used for fermentation and culture production.

REFERENCE SIGNS LIST

1 Hydrogen source gas
2 Air
3 Source gas containing hydrogen and nitrogen
4 Ammonia-containing gas
5, 9, 15 Recovered gas
6 Concentrated ammonia
7 Water
8 Ammonia water
12 Water removed by ammonia stripping apparatus
13 Air
14 Organic compound or microorganism
101 Hydrogen/nitrogen production apparatus
102 Ammonia synthesis apparatus
103 Ammonia concentration apparatus
104, 105 Gas separation membrane
106 Cooler
107 Dehydrator
108 Drier
201 Ammonia water production apparatus
203 Culture apparatus
204 Premixer
205 Ammonia stripping apparatus
1000, 1001, 1002, 1003 Production system for organic compound or microorganism

The invention claimed is:

1. A method of production for a product selected from the group consisting of an organic compound and a microorganism, the method comprising:

reacting a source gas comprising hydrogen and nitrogen in the presence of a ruthenium catalyst and a support, wherein said reacting occurs under conditions comprising a reaction temperature of 530° C. or lower and a reaction pressure of 3 MPa or lower, and wherein an ammonia-containing gas is synthesized;

concentrating ammonia within the ammonia-containing gas to obtain liquid ammonia without obtaining ammonia water or adsorbing ammonia to an absorbent;

premixing the ammonia-containing gas with a medium and recovering unreacted hydrogen and nitrogen therefrom, and recycling said unreacted hydrogen and nitrogen to repeat said reacting; and culturing a microorganism able to produce an organic compound using the liquid ammonia and the medium.

2. The method according to claim 1, wherein said reacting, concentrating, and culturing are successively performed.

3. The method according to claim 1, wherein said reacting occurs under conditions comprising a reaction temperature of 450° C. or lower and a reaction pressure of 1 MPa or lower.

4. The method according to claim 1, wherein the recycling comprises performing dehydration treatment and/or drying treatment to remove water from said unreacted hydrogen and nitrogen.

5. The method according to claim 1, wherein said liquid ammonia is used as a nitrogen source or a pH adjuster in said culturing.

6. The method according to claim 1, wherein the microorganism is able to produce an organic compound selected from the group consisting of amino acids, organic acids, polysaccharides, proteins, antibiotics, and alcohols.

7. The method according to claim 1, wherein the microorganism is a bacterium or a fungus.

* * * * *